US011453851B2

(12) United States Patent
Zumbrunnen et al.

(10) Patent No.: US 11,453,851 B2
(45) Date of Patent: Sep. 27, 2022

(54) GAS SUPPLY DEVICE

(71) Applicant: ADOLF KÜHNER AG, Birsfelden (CH)

(72) Inventors: Simon Paul Zumbrunnen, Oberburg (CH); Tim Bürgin, Liestal (CH); Tibor Anderlei, Müllheim (DE)

(73) Assignee: ADOLF KÜHNER AG, Birsfelden (CH)

( * ) Notice: Subject to any disclaimer, the term of this patent is extended or adjusted under 35 U.S.C. 154(b) by 328 days.

(21) Appl. No.: 16/963,742

(22) PCT Filed: Oct. 15, 2019

(86) PCT No.: PCT/EP2019/077858
§ 371 (c)(1),
(2) Date: Jul. 21, 2020

(87) PCT Pub. No.: WO2020/114655
PCT Pub. Date: Jun. 11, 2020

(65) Prior Publication Data
US 2021/0095236 A1 Apr. 1, 2021

(30) Foreign Application Priority Data
Dec. 6, 2018 (DE) ...................... 10 2018 131 184.2

(51) Int. Cl.
*C12M 1/00* (2006.01)
*C12M 1/24* (2006.01)
*C12M 3/06* (2006.01)

(52) U.S. Cl.
CPC ............ *C12M 23/38* (2013.01); *C12M 23/08* (2013.01); *C12M 27/16* (2013.01); *C12M 29/04* (2013.01); *C12M 29/26* (2013.01)

(58) Field of Classification Search
CPC ...... C12M 23/38; C12M 23/08; C12M 27/16; C12M 29/04; C12M 29/26;
(Continued)

(56) References Cited

U.S. PATENT DOCUMENTS 4,136,796 A 1/1979 Dubois
5,391,496 A 2/1995 Kayal
(Continued)

FOREIGN PATENT DOCUMENTS

DE 3628930 A1 5/1988
DE 69426250 T2 6/2001
(Continued)

OTHER PUBLICATIONS

English Translation of International Preliminary Report On Patentability dated Jun. 8, 2021, 5 Pages.

*Primary Examiner* — Liban M Hassan
(74) *Attorney, Agent, or Firm* — Lucas & Mercanti, LLP

(57) ABSTRACT

A gas supply device for operation in an incubator allowing treatment of a culture within a shaker flask with gas independently of the composition and humidity of the gas atmosphere within the incubator individually supplies each shaker flask of the incubator with gas using a gas supply clamp detachably connected to the closure cap of each flask. The gas supply clamp has at least two elastic clamping jaws and a web connecting the clamping jaws to one another. The clamping jaws exert a clamping force on the side wall of the closure cap. The clamp is held in place by the elastic clamping jaws. Above a sterile filter in the closure cap, an individual gas atmosphere for treatment of the culture in the shaker flask is produced in a recess of the web above a gas passage in the closure cap.

16 Claims, 3 Drawing Sheets

(58) Field of Classification Search
CPC ......... B01L 2300/0681; B01L 3/50825; B01L 3/10; B01L 3/12; B01L 2300/047; B01L 2300/048
USPC ...................................................... 435/304.1
See application file for complete search history.

(56) References Cited

U.S. PATENT DOCUMENTS

| | | | |
|---|---|---|---|
| 2002/0185186 | A1 | 12/2002 | Juliar |
| 2008/0032396 | A1* | 2/2008 | Chokshi ................ C12M 33/14 435/296.1 |
| 2009/0152744 | A1* | 6/2009 | Mou ...................... C12M 27/20 261/119.1 |
| 2015/0218501 | A1* | 8/2015 | Kauling ................ C12M 29/20 435/325 |

FOREIGN PATENT DOCUMENTS

| | | | |
|---|---|---|---|
| EP | 0905229 | A2 | 3/1999 |
| GB | 2214498 | A | 9/1989 |
| JP | 2006204263 | A | 8/2006 |

* cited by examiner

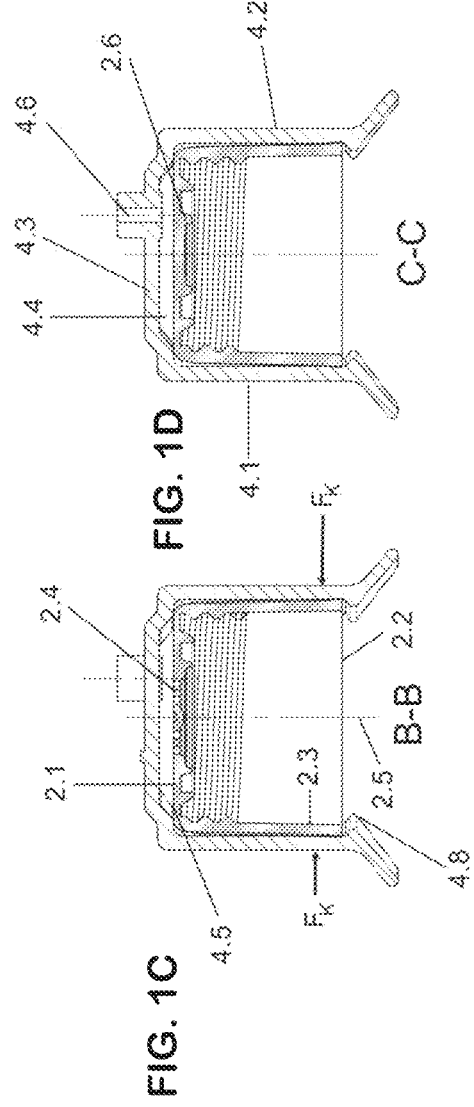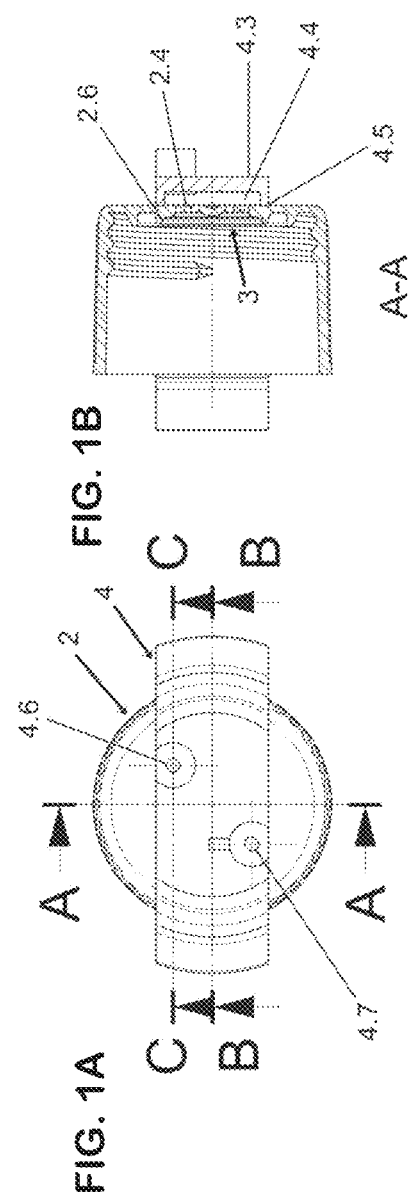

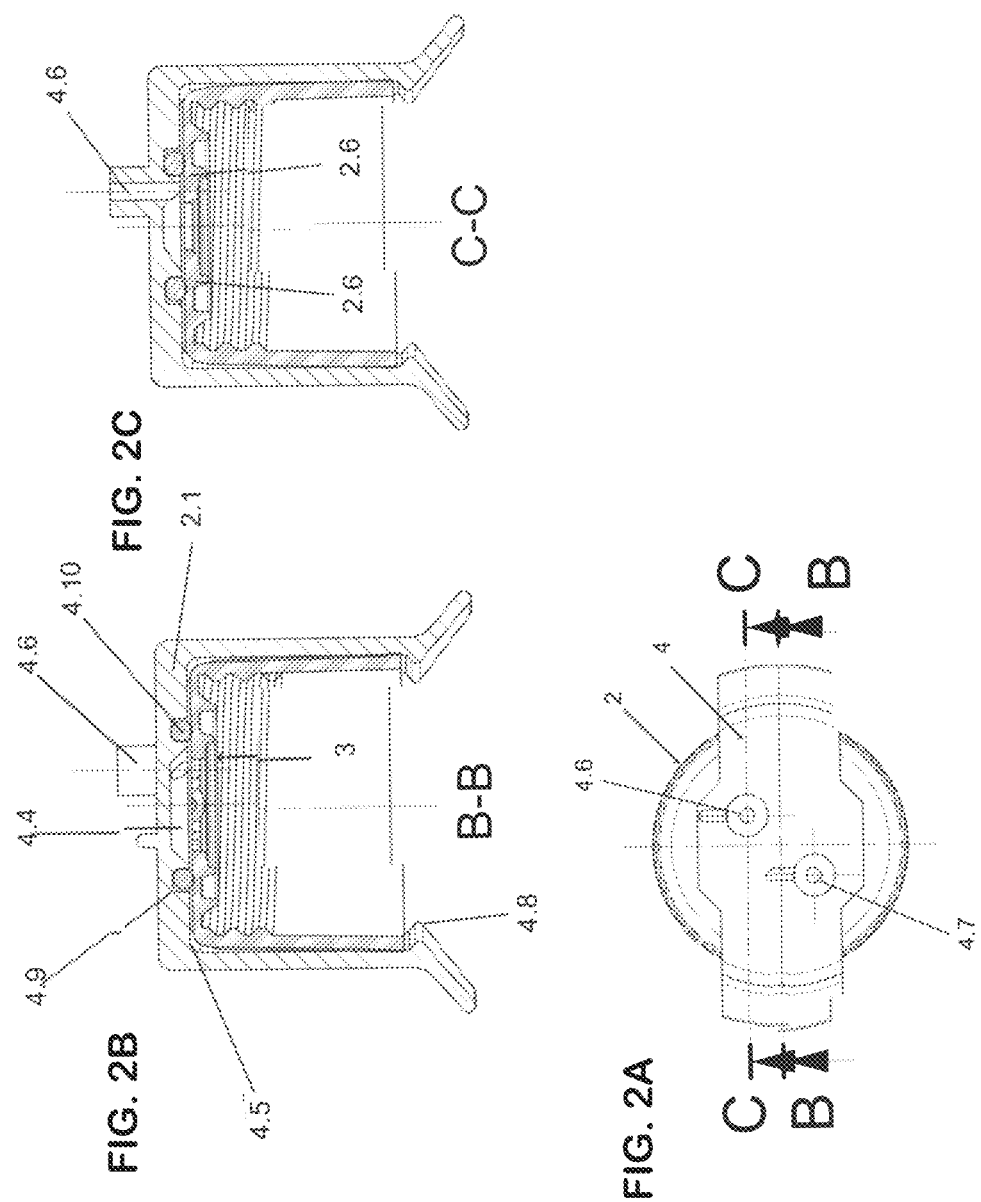

GAS SUPPLY DEVICE

CROSS-REFERENCE TO RELATED APPLICATIONS

This application is a 371 of PCT/EP2019/077858, filed Oct. 15, 2019, which in turn claims the priority of DE 10 2018 131 184.2 filed Dec. 6, 2018. The priority of both applications is hereby claimed and both applications are incorporated herein by reference.

BACKGROUND OF THE INVENTION

The invention relates to a gas supply device for a shaker flask.

Growing cultures using shaker flasks in shaking incubators under predetermined conditions, for example a particular temperature and moisture content, and also a defined gas atmosphere is known from the prior art. The company Adolf Kühner AG Dinkelbergstr. 1, 4127 BIRSFELDEN (Basle), Switzerland, produces, inter alia, such a shaking incubator under the designation ISF1-X.

Treatment with various gases or gas mixtures is necessary, in particular, in the automated determination of process parameters of microbial, biochemical, enzymatic and chemical reactions of cultures and also plant, animal and human cells in shaker flasks which are shaken without interruption until the reaction is concluded. Parameters determined for the cultures are, for example, the oxygen transfer rate (OTR) and the carbon dioxide transfer rate (CTR) and the parameters respiration quotient (RQ) and maximum specific growth rate ($\mu_{max}$) are derived therefrom.

For supply with gas in the incubator, the shaker flasks in each case have a closure cap having a top, in which a gas passage is arranged, adjoining a side wall. Underneath the gas passage, there is a sterile filter on the inside of the top. The culture within the shaker flask is supplied with gas through the passage. The treatment for the gas is usually effected by means of a mixture of carbon dioxide and air. Cultivation within the incubator requires maintenance of the temperature, humidity and composition of the defined gas atmosphere within the incubator. If the incubator is open during cultivation, the temperature, humidity and composition of the gas atmosphere within the incubator and consequently within the shaker flasks supplied with gas can change.

BRIEF SUMMARY OF THE INVENTION

Proceeding from this prior art, it is an object of the invention to provide a gas supply device for a shaker flask for operation in an incubator, which device allows supply of gas to the culture within the shaker flask independently of the composition and humidity of the gas atmosphere within the incubator.

The achievement of this object is based on the idea of supplying gas individually and independently of the humidity and composition of the gas atmosphere in the incubator to each shaker flask via a simple-to-handle gas supply clamp which is connected detachably to the closure cap.

The decoupling of the gas supply to each shaker flask is effected by means of a gas supply clamp which is connected detachably to the closure cap of the shaker flask and has at least two elastic clamping jaws and a web connecting the clamping jaws to one another, with the clamping jaws exerting a clamping force on the side wall of the closure cap. The clamp can be placed without problems on top of the closure cap and is securely held in place by the elastic clamping jaws. The web of the gas supply clamp has a recess on its inside, with the recess being arranged above the gas passage in the closure cap when the gas supply clamp is correctly placed on top. Together with the sterile filter, the recess sealed against the closure cap forms a gas space. An individual gas atmosphere for treatment of the culture with gas can be produced above the sterile filter in the gas space in the respective shaker flasks by means of an inlet for introduction of gas into the recess and an outlet for exit of gas from the recess.

The shaker flask is connected to a gas supply, preferably a gas mixing station, via the inlet for introduction of gas. The gas mixing station is connected to a plurality of gas sources for different gases. The gas sources are, for example, pressurized gas bottles for air, oxygen, carbon dioxide and nitrogen. In order to set the humidity of the gas or of the gas mixture in the shaking flask, a wash bottle is preferably installed in the conduit between the inlet of the shaker flask and the gas mixing station. The gas or gas mixture introduced from the gas mixing station is forced by means of an immersed tube to bubble through a liquid in the gas wash bottle before it leaves the vessel again and is introduced via the inlet into the recess in the gas supply clamp.

If in the case of parallel cultivation of a plurality of cultures in one incubator, one of the shaker flasks is taken from the incubator, this has virtually no influence on the supply of gas to the cultures in the other shaker flasks. Although the temperature changes slightly on opening the door of the incubator, this small temperature change does not have any influence on the cultures in the other shaker flasks.

There are also cultures which have to be grown in a gas atmosphere having a low oxygen content, for example 5%. Such cultures can advantageously be cultivated using the gas supply device of the invention because the increase in the oxygen concentration to the values of the ambient air which would otherwise inevitably occur on opening the incubator can be avoided. To maintain the gas atmosphere in a shaker flask to be taken out, the inlet and outlet thereof can be closed by means of a shut-off valve. Maintenance of low oxygen concentrations is, for example, necessary in the cultivation of stem cells or of microaerophilic microorganisms.

As a result of the humidity of the gas atmosphere in each shaker flask which is individually supplied with gas being set by means of a wash bottle, the atmospheric humidity in the interior space of the incubator can be lower. The lower humidity in the interior space of the incubator increases its life.

Good sealing of the interior space of the shaker flask against the surrounding atmosphere and also secure fastening of the closure cap to the shaker flask is, in an advantageous embodiment of the invention, achieved by the closure cap being configured as a screw closure. The screw closure at the same time allows simple fastening of a circular sterile filter which is clamped along its circumferential periphery between the upper periphery of the neck of the shaker flask and the inside of the top of the closure cap. This fastening at the same time effects sealing of the sterile filter against the inside of the top of the closure cap.

In another embodiment of the invention, a holder for accommodating the sterile filter is arranged on the inside of the closure cap. The holder preferably surrounds the gas passage in a ring-like manner and accommodates the sterile filter flush against its circumferential periphery. In this way, the sterile filter is not only fastened against the inside of the top of the closure cap underneath the gas passage but is at the same time sealed against the inside of the top. The holder extending from the inside of the top into the closure cap can be produced in one operation during injection molding of the closure cap.

A gas supply clamp, which can likewise be simply produced during the course of the injection molding and is also easy to handle, has two diametrically opposite clamping jaws.

When the curvature of the clamping jaws is matched to the curvature of the usually cylindrical side wall of the closure cap, the gas supply clamp can be placed on top in any rotary position relative to the longitudinal central axis of the closure cap and be turned relative to the closure cap. This allows alignment of the inlet and outlet of the gas supply clamp taking into account the spatial circumstances in the incubator and also the gas supply conduits.

To prevent the gas supply clamp from slipping off from the closure cap and at the same time to generate an initial stress between the web of the gas treatment clamp and the top of the closure cap at moderate clamping forces on the side wall of the closure cap, each clamping jaw preferably has a latching nose which reaches behind an opening-side periphery of the closure cap. The prestressing is necessary in order to ensure sufficient sealing of the recess of the gas supply clamp against the outside of the closure cap.

When the recess completely covers the gas passage, the gas exchange through the gas passage in the closure cap is improved. A smooth, i.e., planar/flat, periphery which completely surrounds the recess can effectively seal the recess against the outside.

A further-improved gas tightness is achieved by an O-ring surrounding the recess being arranged between the top and the web of the gas supply clamp as seal for the recess against the outside of the top of the closure cap. The O-ring is preferably let into a circumferential groove on the inside of the web. The groove is preferably let into a smooth periphery which completely surrounds the recess.

In an advantageous embodiment of the invention, the recess and the gas passage are arranged flush to the longitudinal central axis of the closure cap. If both the recess and the gas passage have a circular cross section, a rotationally symmetric gas space in which a uniform microclimate is formed above the sterile filter, is created by the alignment relative to the longitudinal central axis.

Arrangement of the inlet and outlet diametrically to the longitudinal central axis of the closure cap contributes to the microclimate being made ever more uniform. The inlet and outlet are, in particular, configured as hollow-cylindrical passages which open into the recess. The cylindrical axes of the passages run parallel to the longitudinal central axis at as great a distance as possible.

The following explains the invention in more detail using the figures.

BRIEF DESCRIPTION OF THE DRAWINGS

The figures show
FIG. 1A a plan view of a first working example of a gas supply device according to the invention,
FIG. 1B a section along the line A-A in FIG. 1a,
FIG. 1C a section along the line B-B in FIG. 1a,
FIG. 1D a section along the line C-C in FIG. 1a,
FIG. 2A a plan view of a second working example of the gas supply device of the invention,
FIG. 2B a section along the line B-B in FIG. 2a,
FIG. 2C a section along the line C-C in FIG. 2a, and
FIG. 3 a schematic depiction of a shaking incubator with a plurality of shaker flasks which are equipped with gas supply devices according to the invention.

DETAILED DESCRIPTION OF THE PREFERRED EMBODIMENTS

Figure 3:
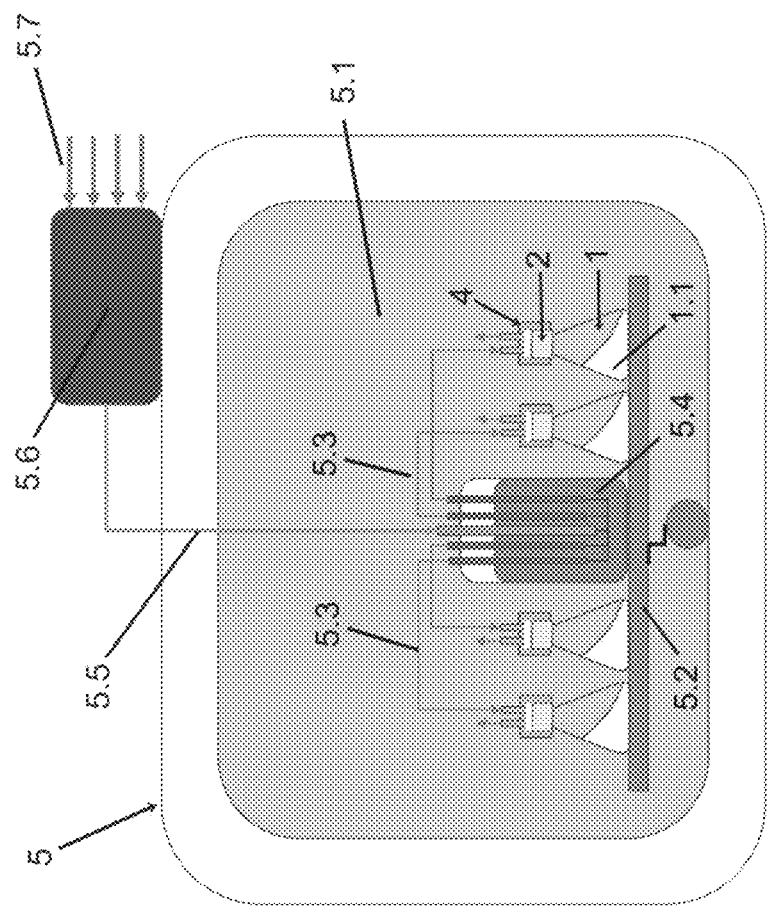

The gas supply device for a shaker flask (1) comprises a hollow-cylindrical closure cap (2) which is configured as screw closure and has a top (2.1), a lower opening (2.2) opposite the top (2.1) and also a side wall (2.3) extending between the top (2.1) and the lower opening (2.2). A gas passage (2.4) which can be seen in FIGS. 1B and 1C is arranged in the top (2.1) concentrically with the longitudinal axis (2.5) of the closure cap (2). The gas passage (2.4) has radial and ring-like stiffening elements which are produced in one piece with the closure cap (2) as injection-molded part.

On the inside of the closure cap (2) a holder (2.6) which surrounds the gas passage (2.4) in a ring-like manner is injection-molded onto the inside of the closure cap (2) and accommodates a sterile filter (3) in a flush manner. The molded-on holder (2.6) at the same time seals the sterile filter from the inside of the top (2.1) of the closure cap (2).

A gas supply clamp (4) is detachably connected to the closure cap (2). FIGS. 1 and 2 in each case show a closure cap (2) which is correctly connected to the gas supply clamp (4). The gas supply clamp (4) has two diametrically opposite, elastic clamping jaws (4.1, 4.2) and a web (4.3) which connects the two clamping jaws to one another, with the clamping jaws (4.1, 4.2) exerting a clamping force (FK) on the side wall (2.3) of the closure cap (2).

The web (4.3) has an inside facing the outside of the top (2.1) of the closure cap (2). On the inside of the web (4.3), there is a recess (4.4) above the gas passage (2.4). As can be seen in particular, from FIG. 10 in combination with FIG. 1B, the recess (4.4) completely covers the gas passage (2.4). A smooth, i.e., planar/flat, periphery (4.5) completely surrounds the recess (4.4), with the smooth periphery (4.5) running in a straight line in the longitudinal direction of the web (4.3), as can be seen from FIG. 1B, and in a curved manner in the transition region to the clamping jaws (4.1, 4.2). The smooth periphery (4.5) lies flush against the flat outside of the top (2.1) of the closure cap (2) and thus seals the recess (4.4) against the closure cap (2).

Two cylindrical passages open into the recess (4.4) of the gas supply clamp (4), with one of the two passages forming an inlet (4.6) for introduction of gas into the recess (4.4) and the other passage forming an outlet (4.7) for exit of gas from the recess (4.4).

As can be seen, in particular, from the plan view in FIG. 1A, the curvature of the clamping jaws (4.1, 4.2) is matched to the curvature of the side wall (2.3), which has a circular cross section, of the closure cap (2). The two clamping jaws (4.1, 4.2) are chamfered outward at their lower, free ends. In the region of the chamfer, each clamping jaw (4.1, 4.2) has a latching nose (4.8) which reaches behind the periphery of the lower opening (2.2) of the closure cap (2).

The gas supply device shown in FIG. 2 has a structure corresponding to that of the gas supply device of FIG. 1. Corresponding components are therefore provided with the same reference numerals. However, there are differences in respect of the shape of the recess (4.4) and the way in which it is sealed against the outside of the top (2.1) of the closure cap (2). The recess (4.4) has a circular cross section which is completely surrounded by a smooth periphery (4.5) which surrounds the recess (4.4) in a ring-like manner. In the smooth periphery, a ring-like circumferential groove (4.9) is let into the web (4.3). The groove (4.9) accommodates an O-ring (4.10) which seals the recess (4.4) against the outside of the top (2.1).

In order to make the distance from the passages forming the inlet (4.6) and the outlet (4.7) to the longitudinal central axis (2.5) of the closure cap (2) as great as possible, the passages open into the side walls of the recess (4.4) which widen conically from the base of the recess.

FIG. 3 shows a shaking incubator (5) having an interior space (5.1) in which four shaker flasks (1), which are equipped with a gas supply device according to the invention comprising a closure cap (2) and a gas supply clamp (4), are fixed on a shaker (5.2). The inlets (4.6) of the four shaker flasks (1) are connected in a gas-conducting manner via tubing (5.3), which is shown purely schematically, to a gas distributor and gas scrubber (5.4). The gas distributor and gas scrubber (5.4) is connected via a gas feed conduit (5.5) to a gas mixing station (5.6) which mixes the gas from a plurality of gas sources (5.7) for various gases or gas mixtures, for example air, nitrogen, oxygen and carbon dioxide, according to the gas atmosphere required for the treatment with gas. Such gas mixing stations (5.6) are known per se and are supplied, for example, by the company Adolf Kühner AG, Dinkelbergstrasse 1, CH-4127 Birsfelden (Basle) under the designation FlowCon 2/3/4 (cf. Kuhner shaker, FlowCon 2/3/4 Stand-alone gas mixing device, https://www.kuhner.com/de/produkte/anwendungstechnologien/gas-mixing/flowcon-234.html, downloaded on Nov. 30, 2018).

The gas mixing station (5.6) and the gas sources (5.7) are arranged outside the shaking incubator (5); only the gas feed conduit (5.5) penetrates through the wall of the shaking incubator (5). The gas or the gas mixture goes via the gas feed conduit (5.5) to the gas distributor and gas scrubber (5.4). This distributes the gas, independently of the gas atmosphere in the interior space (5.1) of the shaking incubator (5), via the conduits (5.3) to the gas supply devices of the individual shaker flasks (1).

In the gas space above the sterile filter (3) of the gas supply device of each shaker flask (1), a microclimate which has the introduced gas composition and the humidity set by means of the gas distributor and gas scrubber (5.4) is established. Cultivation of the culture media (1.1) in the shaker flasks (1) occurs under the action of this microclimate. If a shaker flask (1) is taken out from the shaking incubator (5), this removal has virtually no influence on the parallel cultures. The slight decrease in the temperature in the interior space (5.1) caused by opening of the incubator door has virtually no effect on the cultivation of the culture media (1.1) in the remaining shaker flasks (1). Due to the gas supply clamp (4) which is particularly easy to handle and can be detached from the closure caps (2), each shaker flask can be provided in a simple way with a gas supply device according to the invention.

If the gas atmosphere in the shaker flask (1) is to be maintained for the culture after detachment of the gas supply device of the invention from the conduit (5.3), both the inlet and the outlet (4.6, 4.7) can, in an embodiment of the invention which is not shown, in each case be provided with a shut-off valve.

For this purpose, manually actuatable shut-off valves or pinch valves on tubings, which are connected to the inlet or outlet, can be provided.

List of reference numerals

| No. | Name |
|---|---|
| 1 | Shaker flask |
| 1.1 | Culture media |
| 2 | Closure cap |
| 2.1 | Top |
| 2.2 | Lower opening |
| 2.3 | Side wall |
| 2.4 | Gas passage |
| 2.5 | Longitudinal central axis |
| 2.6 | Holder |
| 3 | Sterile filter |
| 4 | Gas supply clamp |
| 4.1 | Clamping jaw |
| 4.2 | Clamping jaw |
| 4.3 | Web |
| 4.4 | Recess |
| 4.5 | Smooth periphery |
| 4.6 | Inlet |
| 4.7 | Outlet |
| 4.8 | Latching nose |
| 4.9 | Groove |
| 4.10 | O-Ring |
| 4.11 | Lateral wall |
| 5 | Shaking incubator |
| 5.1 | Interior space |
| 5.2 | Shaker |
| 5.3 | Conduits |
| 5.4 | Gas distributor and gas scrubber |
| 5.5 | Gas feed conduit |
| 5.6 | Gas mixing station |
| 5.7 | Gas sources |

The invention claimed is:

1. A gas supply device for a shaker flask, comprising:
a hollow-cylindrical closure cap having a top, a lower opening, and a side wall extending between the top and the lower opening, wherein the top has a gas passage therethrough;
a sterile filter arranged on and sealed against an inside of the top underneath the gas passage,
a gas supply clamp connected detachably to the closure cap, the gas supply clamp having two elastic clamping jaws and a web connecting the clamping jaws to one another, the clamping jaws exerting a clamping force on the side wall of the closure cap,
the web having a recess arranged above the gas passage, a seal for the recess against an outside of the top, an inlet for introduction of gas into the recess, and an outlet for exit of gas from the recess.

2. The gas supply device as claimed in claim 1, wherein the closure cap is configured as screw closure.

3. The gas supply device as claimed in claim 1, further comprising a holder accommodating the sterile filter arranged on the inside of the top of the closure cap.

4. The gas supply device as claimed in claim 3, wherein the holder has a circumferential periphery, the holder is configured to surround the gas passage, and the sterile filter is accommodated flush against the circumferential periphery.

5. The gas supply device as claimed in claim 1, wherein the two clamping jaws of the gas supply clamp are diametrically opposed clamping jaws.

6. The gas supply device as claimed in claim 1, wherein a curvature of the clamping jaws is matched to a curvature of the side wall of the closure cap.

7. The gas supply device as claimed in claim 1, wherein each of the clamping jaws has a latching device which at least partially overlies a periphery of the lower opening of the closure cap.

8. The gas supply device as claimed in claim 1, wherein the recess completely overlaps the gas passage.

9. The gas supply device as claimed in claim 1, wherein a planar/flat periphery completely surrounds the recess.

10. The gas supply device as claimed in claim 1, wherein an O-ring surrounding the recess is arranged between the top and the web as the seal for the recess against the outside of the top.

11. The gas supply device as claimed in claim 1, wherein the recess and the gas passage are aligned with a longitudinal central axis of the closure cap.

12. The gas supply device as claimed in claim 1, wherein the inlet and the outlet are arranged diametrically to a longitudinal central axis of the closure cap.

13. The gas supply device as claimed in claim 1, further comprising a gas mixing station and a conduit connecting the gas mixing station to the inlet.

14. The gas supply device as claimed in claim 13, further comprising a wash bottle inserted in the conduit between the gas mixing station and the inlet.

15. The gas supply device as claimed in claim 1, wherein the inlet and/or the outlet is closable by a shut-off valve.

16. A shaking incubator having an interior space in which a plurality of shaker flasks having a gas supply device as claimed in claim 1 are arranged.

* * * * *